United States Patent
Sliwa et al.

(10) Patent No.: US 10,219,702 B2
(45) Date of Patent: Mar. 5, 2019

(54) SINGLE FIBER FORCE-SENSING OF BOTH AXIAL AND BENDING CATHETER TIP FORCES

(71) Applicant: St. Jude Medical, Cardiology Division, Inc., St. Paul, MN (US)

(72) Inventors: John W. Sliwa, Los Altos Hills, CA (US); Joseph M. Schmitt, Andover, MA (US); Yu Liu, Irvine, CA (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 955 days.

(21) Appl. No.: 14/668,574

(22) Filed: Mar. 25, 2015

(65) Prior Publication Data
US 2015/0272443 A1 Oct. 1, 2015

Related U.S. Application Data

(60) Provisional application No. 61/970,735, filed on Mar. 26, 2014.

(51) Int. Cl.
*A61B 5/00* (2006.01)

(52) U.S. Cl.
CPC .......... *A61B 5/0084* (2013.01); *A61B 5/6885* (2013.01); *A61B 2562/0238* (2013.01)

(58) Field of Classification Search
None
See application file for complete search history.

(56) References Cited

U.S. PATENT DOCUMENTS

| 7,386,339 | B2 | 6/2008 | Strommer et al. | |
|---|---|---|---|---|
| 8,048,063 | B2 | 11/2011 | Aeby et al. | |
| 8,157,789 | B2 | 4/2012 | Leo et al. | |
| 8,435,232 | B2 | 5/2013 | Aeby et al. | |
| 8,622,935 | B1 * | 1/2014 | Leo | A61B 5/6843 600/585 |
| 2009/0254078 | A1 | 10/2009 | Just et al. | |
| 2011/0270046 | A1 | 11/2011 | Paul et al. | |
| 2012/0265102 | A1 | 10/2012 | Leo et al. | |
| 2013/0100439 | A1 * | 4/2013 | Yu | G01N 21/255 356/73 |
| 2015/0272443 | A1 * | 10/2015 | Sliwa | A61B 5/0084 600/478 |

OTHER PUBLICATIONS

Hill et al., "SU-8 MEMS Fabry-Perot pressure sensor". Sensors and Actuators A 138 (2007). pp. 52-62.*
Ming Han, "Theoretical and Experimental Study of Low-Finesse Extrinsic Fabry-Perot Interferometric Fiber Optic ensors," PhD Thesis Dissertation, May 2006, 142 pages, Blacksburg, Virginia.

* cited by examiner

*Primary Examiner* — James Kish
(74) *Attorney, Agent, or Firm* — Dykema Gossett PLLC

(57) ABSTRACT

A single optical fiber force-sensing assembly includes a catheter configured to detect both axial and bending tip displacement. The catheter includes a flexible structure located adjacent to a distal tip portion of the catheter. The single optical fiber within the catheter defines a first reflective surface. A second reflective surface is located closely adjacent to the first reflective surface.

17 Claims, 11 Drawing Sheets

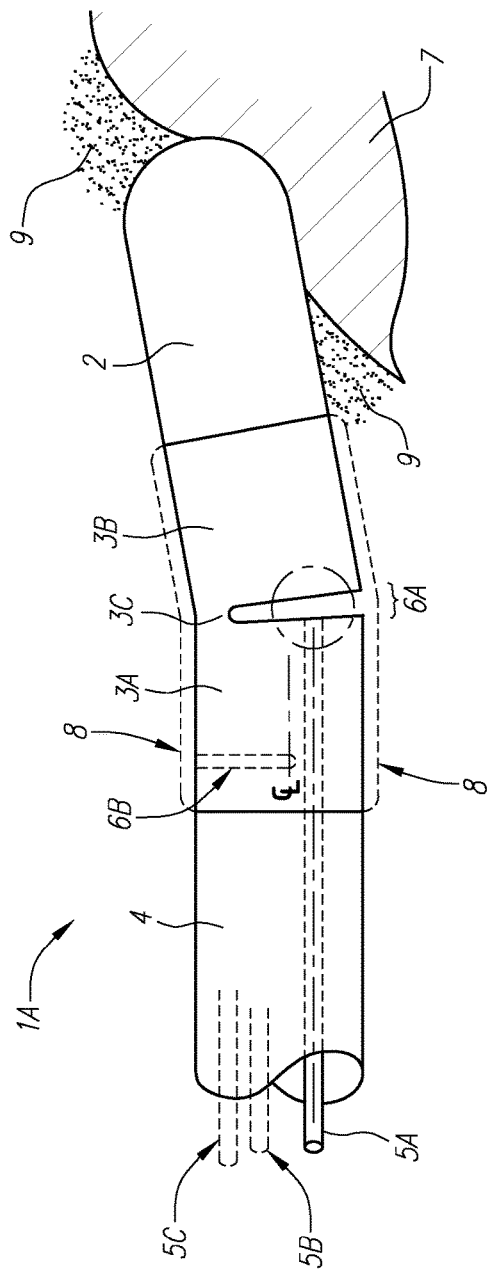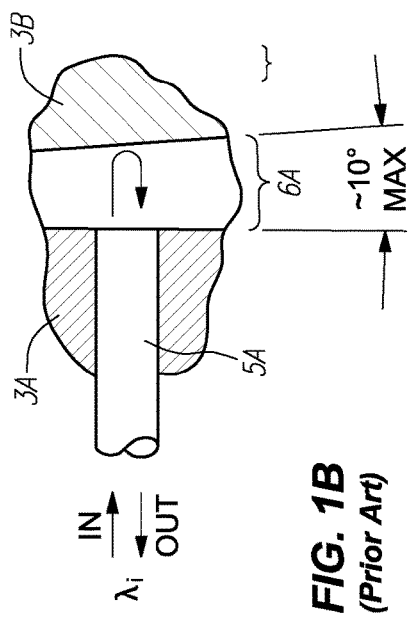
FIG. 1A
*(Prior Art)*
FIG. 1B
*(Prior Art)*

SINGLE FIBER FORCE-SENSING OF BOTH AXIAL AND BENDING CATHETER TIP FORCES

CROSS-REFERENCE TO RELATED APPLICATIONS

This application claims priority to U.S. provisional application No. 61/970,735 filed 26 Mar. 2014 (the '735 application). The '735 application is hereby incorporated by reference as though fully set forth herein.

BACKGROUND OF THE DISCLOSURE a. Field of the Disclosure

The instant disclosure relates generally to a force-sensing catheter, and particularly to a single-optical fiber force-sensing catheter configured to detect both axial and bending tip displacement.

b. Background Art

The visualization and treatment of organs and tissues has been advanced through the increasing use of catheter systems. Catheter systems have been designed for the incorporation of various components to treat and diagnose ailments, as accomplished through the mapping of organs, sensing of thermal and electrical changes exhibited by a tissue (e.g., heart), as well as the application of energizing sources (such as radiofrequency (RF), cryogenics, laser, and high frequency ultrasound) to tissue. Moreover, catheter systems may be further modified to include irrigation channels that enable cooling of the electrode tip during ablation procedures.

Catheter systems generally include a portion that contacts the tissue or organ, or is inserted in an environment (e.g., heart chamber or vessel) to detect a number of parameters, such as for example, location of the tissue, contact or pressure exerted on the tissue, electrophysiological attributes of the tissue, or other type of parameters that aid in the evaluation or treatment of the organ or tissue.

Sufficient contact between a catheter, in particular an electrode provided in connection with a catheter, and tissue during a procedure is generally preferred to ensure that the procedure is effective and safe. Current techniques of mapping, visualization and treatment using energizing sources, such as the use of radiofrequency energy during ablation, rely on placing the electrode of a catheter system in consistent mechanical contact with targeted tissue. Lesion formation (such as lesions created by exposure to radiofrequency) partially depends upon the direction of contact between the electrode and tissue. For example, for endocardial catheter applications, the point of electrode-tissue contact may be on the order of 150 cm away from the point of application of force applied by the operator (whether manual or automated) of the catheter outside of the body. Coupled with the fact that a beating heart has dynamically moving walls, this gives rise to some functional and theoretical challenges, such as ensuring that the electrode is in sufficiently constant physical contact with the myocardial wall, while also avoiding or minimizing the risk of perforation of the cardiac wall.

Catheter systems having sensor assemblies, such as those mounted on the catheter shaft proximal to the electrode or remotely in the handle set, leave the possibility, however small, of obtaining false positive outcomes when detecting contact between the electrode and the tissue. False positive outcomes may occur, for example, when a nonconductive portion of the catheter wall, and not the electrode, is in contact with the tissue. Such condition may arise during the catheter manipulation in the heart when, for instance, the distal portion of the catheter is curled inward so much as to lose electrode contact with the tissue, while the proximal portion of the catheter is in contact with the tissue. When this happens, remotely placed sensors can generate signals due to the deflection of the catheter shaft, thereby falsely indicating contact between the electrode and tissue. Accordingly, optic-based contact sensors associated with the electrode can, among other things, help reduce the possibility of obtaining false positive outcomes when detecting contact between the electrode and the tissue.

SUMMARY

A single optical fiber force-sensing assembly includes a catheter configured to detect both axial and bending tip displacement. The catheter includes a flexible structure located adjacent to a distal tip portion of the catheter. The single optical fiber within the catheter defines a first reflective surface. A second reflective surface is located closely adjacent to the first reflective surface.

A force-sensing assembly in accordance with one embodiment of the present teachings includes: a catheter shaft comprising a proximal section and a distal section, the distal section comprising a distal tip portion; a flexible structure located adjacent the distal tip portion, the flexible structure having a calibratable stiffness; a single optical fiber extending longitudinally along at least a portion of the catheter shaft and defining a first Fabry-Perot reflective surface adjacent to the flexible structure, the single optical fiber configured to detect optical interference data; and a second Fabry-Perot reflective surface located closely adjacent to the first Fabry-Perot reflective surface, wherein the first and second Fabry-Perot reflective surfaces are separated by a gap comprising part of the flexible structure and configured to facilitate relative movement between the first and second Fabry-Perot reflective surfaces when the distal section of the catheter shaft is deflected.

A force-sensing catheter in accordance with another embodiment of the present teachings includes: (a) a catheter shaft comprising a proximal section and a distal section, the distal section comprising a distal tip portion; and (b) a flexible structure located adjacent to the distal tip portion, wherein the flexible structure comprises: (i) a compliant section comprising a first portion, a second portion, and a compressible-and-deflectable region separating the first portion from the second portion and configured to facilitate relative movement between the first portion and the second portion; (ii) an optical fiber mounted for movement within the first portion, wherein the optical fiber comprises a first reflective surface; and (iii) a second reflective surface mounted for movement with the second portion.

A force-sensing assembly in accordance with another embodiment of the present teachings includes: a catheter shaft comprising a proximal section and a distal section, the distal section comprising a distal tip portion; a flexible structure located adjacent the distal tip portion, the flexible structure having a calibratable stiffness; a single optical fiber extending longitudinally along at least a portion of the catheter shaft and defining a first Fabry-Perot reflective surface adjacent to the flexible structure, the single optical fiber configured to detect optical interference data; a second Fabry-Perot reflective surface located closely adjacent to the first Fabry-Perot reflective surface, wherein the first and second Fabry-Perot reflective surfaces are separated by a gap comprising part of the flexible structure and configured to facilitate relative movement between the first and second Fabry-Perot reflective surfaces when the distal section of the catheter shaft is deflected; and a processor configured to use the detected optical interference data and the calibrated stiffness of the flexible structure to determine at least an axial force and a bending force at the distal tip portion of the catheter; wherein the first Fabry-Perot reflective surface and the second Fabry-Perot reflective surface together comprise a Fabry-Perot interferometer; wherein the first and second Fabry-Perot reflective surfaces are separated by a wedge angle between of about 0 degrees and 10 degrees; wherein the detected optical interference data includes a detected optical interference fringe spacing and a detected optical interference fringe visibility; wherein the detected optical interference fringe spacing corresponds to an axial deflection of the distal tip portion of the catheter; and wherein the detected optical interference fringe visibility corresponds to a bending deflection of the distal tip portion of the catheter.

BRIEF DESCRIPTION OF THE DRAWINGS

FIG. 1A is a schematic view of a prior art three-fiber force sensor in a tissue-loaded position, wherein only one of the three fiber sensors located on the catheter periphery is shown for simplicity. The three Fabry-Perot (FP) sensors (one shown) detect axial displacement only, and data from the three different sensors is mathematically converted into bending and axial force magnitudes.

FIG. 1B is a blown-up cut-out view of the single-mode fiber (SMF) FP sensor of FIG. 1A.

DETAILED DESCRIPTION OF THE DISCLOSURE

Figure 2A:
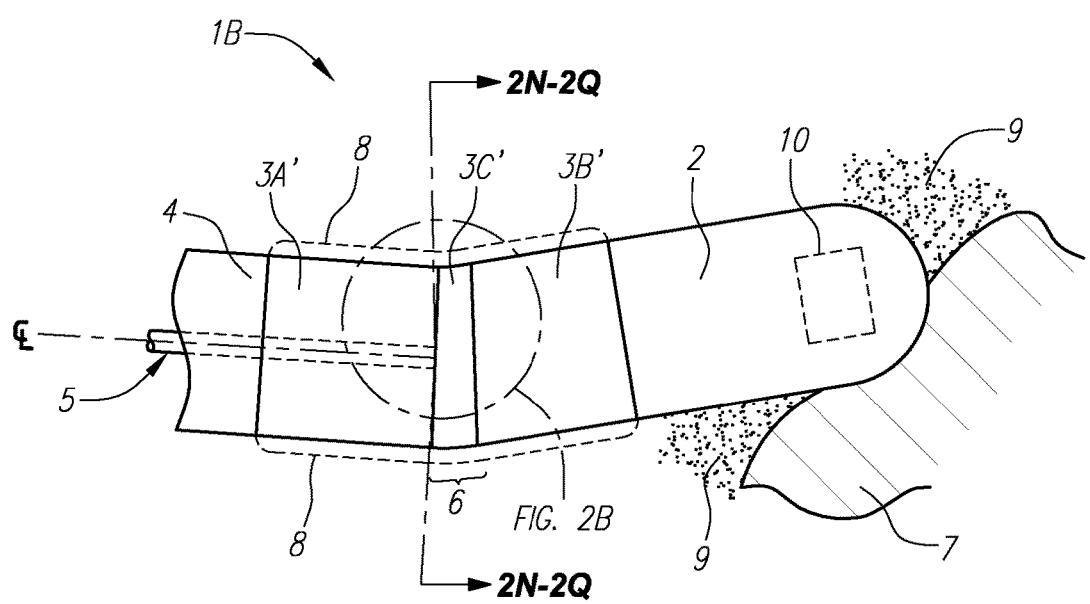
FIG. 2A is a schematic view of an exemplary force-sensing catheter in accordance with the present disclosure, wherein a single SMF or multi-mode fiber (MMF) FP sensor is centrally and axially employed (reduced from the three peripherally located sensors of FIGS. 1A and 1B). The single FP sensor can detect both axial and radial (bending/tilt) displacements using different interference phenomenon, unlike the device of FIGS. 1A and 1B.

The present disclosure relates to a catheter comprising single-mode fiber (SMF) Fabry-Perot (FP) or other optical sensing technology. Current SMF FP sensors, such as those made and owned by St. Jude Medical, Inc., include three peripheral fiber FP subsensors, which consume significant tip space and have a relatively high cost of goods sold (COGS). The disclosure herein provides for a single-optical fiber force-sensing catheter, such as a single-fiber FP force-sensing catheter, which significantly reduces the COGS and provides more space inside the catheter for other sensors, such as lesion-feedback and navigation sensors. Force sensor reliability may also be improved in the disclosed single-fiber FP force-sensing catheter due to the reduced number of components inside the catheter.

Existing tri-axial force sensors include optical sensors and/or magnetic sensors capable of reporting the axial force component (along the catheter axis) and the bending force component (along a reported specific bending axis). The vector sum of the axial force component and the bending force component is the net tip force. Typically, all three forces are reported to a physician or other user of the catheter. Alternatively, only the net force vector may be reported.

The implementation of three such sensors (whether optical, magnetic, etc.), each 120 degrees apart and located at the same radial distance from the center axis, is expensive and space-consuming. Among other things, the present disclosure describes a way to report the axial force and the bending force magnitude using a single force sensor.

The bending force plane of a catheter (defined by the tip and nearby bent catheter lumen) is, on average, approximately locally normal to the tissue upon which it presses. However, the bending force plane may deviate from a true 90 degrees to the tissue if, for example, there is a trough or trabeculation in the tissue. Nevertheless, the true force may still be correctly known in magnitude. It is the net force magnitude which correlates with lesion and procedure efficacy. Thus, a simpler single-sensor force tip (rather than a tri-sensor force tip) catheter can perform with the same efficacy and safety at a much lower disposable complexity and cost.

The present disclosure addresses how to report both axial and bending forces independently, as well as their vector sum. The use of a single magnetic coil pair, would not allow for differentiation between axial and bending deflections. In fact, axial compression would increase coil coupling while bending deflection would decrease coil coupling, leading the two forces to cancel each other out and report zero force despite a significant force being present.

In accordance with the disclosure, for optical displacement sensors, such as FP interferometric displacement sensors, one can independently deduce both axial and bending forces using a single sensor that is preferably centrally axially situated. In the context of a FP sensor, this is possible because axial and bending displacements have different effects on the FP optical interference pattern, regardless of whether SMF or MMF illumination is employed. If total deflection is kept small (e.g. less than about 10 degrees), then a SMF FP sensor can report both axial and bending deflections.

FIG. 1A depicts a prior-art force-sensing catheter 1A with an RF ablation tip 2, a catheter shaft 4, and an intervening flexible structure 3A/3B/3C. For clarity, only one of the three FP sensors (comprising optical fiber 5A and slot 6A) is shown. The flexible structure 3A/3B/3C can be a spring comprising a rod or tube with force-compliant lateral slots, such as slot 6A cut into flexible structure section 3C. The remaining uncut part of flexible structure section 3C adjacent the slot 6A is where the spring bending is concentrated. The gap or slot 6A serves as the sensing cavity of a SMF FP axial displacement sensor. The catheter 1A is shown under blood 9 contacting a tissue target 7 in a force-loaded state. Three optical fibers are shown as fiber 5A (associated with the only depicted FP sensor) and fibers 5B and 5C, both shown in phantom, and both associated with other FP sensors (not shown). Typically, the flexible structure 3A/3B/3C has at least two bendable slots or gaps, such as 6A and 6B (shown in phantom). The flexible structure 3A/3B/3C may be covered by a flexible sleeve 8 (also shown in phantom). The sleeve 8 may be an elastomeric sheath of lower stiffness than flexible structure 3A/3B/3C. One purpose of such a sleeve 8 is to keep saline irrigant inside the catheter 1A and/or to keep blood 9 outside the catheter 1. The slots such as 6A and 6B are arranged such that bends can be sensed in all radial directions. The three optical fibers/FP sensors may be 120 degrees apart and situated near the outer diameter of the catheter, or may be arranged in other manners.

FIG. 1B is a blown-up cut-out view of the SMF FP sensor of FIG. 1A. The sensor comprises the optical fiber 5A and the variable gap 6A, wherein the wall of the gap defined by flexible structure section 3B is reflective, such that light emanating rightwards from fiber 5A is reflected from the mirror/wall flexible structure section 3B. When a maximal force is exerted on the catheter tip 2 (e.g., 40 grams), the tip 2 bends relative to the shaft 4 about 10 degrees maximum. In FIG. 1B the light lambda $\lambda_i$ is depicted traveling rightwards (toward reflective flexible structure section 3B) and leftwards (after reflection(s)) within fiber 5A. The light $\lambda_i$ may bounce several times within the cavity of the FP sensor, providing known FP reflection spectra having interference peaks and minimums. The FP spectra data can be used to compute the cavity 6A dimensional change according to methods known by one of ordinary skill in the art by, for example, measuring the wavelength spacing between interference peaks or valleys.

Continuing with FIGS. 1A and 1B, the prior-art catheter 1A has three SMF FP sensors arranged peripherally and 120 degrees from one another, all at a radius from the catheter center line or central axis. The three fibers 5A/5B/5C consume significant room in the catheter 1, along with flexible structure 3A/3B/3C with compliant side-slots 6A/6B. This makes it difficult to route non-force-sensing wiring or tubing through or past the flexible structure 3A/3B/3C to the most distal tip 2. The force sensor formed from fiber 5A, for example, works by interferometrically detecting the size and angle of gap 6A, as well as dimensional changes of gap 6A under varying load forces. The stiffness of flexible structure 3A/3B/3C is typically characterized in product development; therefore, a detected value for the size or angle of gap 6A can be associated with a particular load force component on the flexible structure 3A/3B/3C. It should be apparent that any 120 degree triaxial force sensor, such as that of FIGS. 1A and 1B, may be used to detect purely axial force as an equal axial deflection of all three FP sensors and to detect bending force as unequal deflections of the three FP sensors. In this manner, the axial force, the bending force, and the bending direction can be derived.

Lesion-implementing efficacy has been demonstrated to correlate to the net force magnitude—i.e., a net force of at least approximately 15-20 grams should be present at all times during use of catheter 1. Nevertheless, the bending direction of the catheter 1 is irrelevant to lesion-implementing efficacy, as the sensed force magnitude is always the true tissue contact force, regardless of whether it is perpendicular to the local tissue. Therefore, graphical depiction of the distal tip 2 resting upon a graphical 3D chamber model can be accomplished in an approximate way by using a single, axially-situated force sensor (rather than three prior-art peripherally situated sensors, as shown in FIGS. 1A and 1B), and by knowing only axial and bending force magnitudes by drawing the net force arbitrarily in a plane perpendicular to the local tissue—i.e., not knowing the true bend force orientation relative to the tissue-normal. Indeed, a trabeculation could easily cause the net force plane to not be perpendicular to the local tissue; however the sensed net force magnitude is still correct and the lesion-efficacy thereby assured. Moreover, a single force sensor (as opposed to three force sensors), whether magnetic or optical in nature, would dramatically reduce the cost, complexity, and tip packaging challenges associated with triaxial force-sensing catheters.

However, for a single optical sensor, such as a single SMF or MMF FP optical sensor, detection of both axial and bending force deflections is possible. An optical sensor can differentiate between axial and bending forces because axial and bending forces have different effects on the interference pattern they generate (unlike magnetic coils, which have only an amplitude effect for both bending and axial tip deflections). The ability of optical sensors to detect bending forces, as well as axial forces, has actually been treated as a problem in the prior art of making optical axial deflection FP detectors (such as those of FIGS. 1A and 1B) because any tilt angle between the two reflective surfaces of the FP sensor systematically reduces the fringe (peak/valley) contrast. (See Han, Ming, PhD Thesis Dissertation of May 2006, "Theoretical and Experimental Study of Low-Finesse Extrinsic Fabry-Perot Interferometric Fiber Optic Sensors," Chapter 2.) Yet, such tilted-reflector "defects" can be taken advantage of as a tilt (bending) sensor, wherein reflector tilting is purposely caused by tip-bending and, therefore, sensor bending. Further, for modest maximum bend angles of up to several degrees (e.g., 0.5-0.8 degrees max for MMF FPs and up to 10 degrees max for SMF FPs), both axial displacement and bending (mirror tilt) displacement can be detected independently. For example, the spectral separation between interference nulls of the interference pattern can still be used to determine sensor gap, which is indicative of axial deflection and, therefore, axial force; whereas the contrast or visibility of the peaks can be independently used to determine reflector tilt angle and, therefore, bending force. Thus, if the total catheter tip deflection remains within the maximum bend angles, a single fiber optical sensor can be used to determine both bending force and axial force.

Figure 2B:
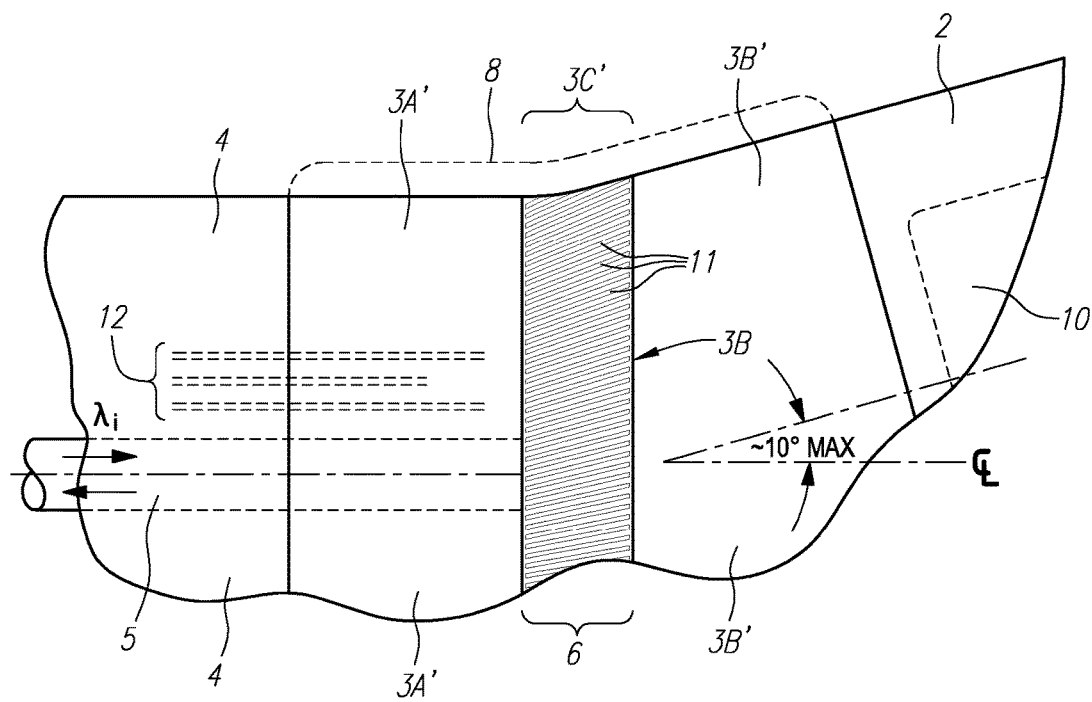
FIG. 2B is an enlarged view of the FP sensor of FIG. 2A showing the central axial location of the single sensor/fiber and the use of a single circumferential laser-etched calibrated spring.

FIGS. 2A and 2B depict an exemplary force-sensing catheter 1B in which a single fiber 5 optical FP sensor is centrally and axially employed. Catheter 1B can have a RF ablator tip 2 and a flexible catheter shaft 4. A force-calibrated flexible structure 3A'/3B'/3C' can be situated between the tip 2 and the shaft 4. An optional elastomeric overlying sheath 8, shown in phantom, may be employed. The single fiber 5 and FP sensor can be situated on the central axis of catheter 1B, and the single FP sensor can be situated radially in the middle of the gap 6. However, in other embodiments, the fiber 5 can be located off-center within the catheter 1B. The fiber 5 can be mechanically embedded within the throat of catheter 1B by a metal or ceramic structure surrounding the fiber 5, or by a plurality of legs, stakes, or similar support structures, for example (see FIGS. 2N-2Q). In an embodiment, the RF ablator tip 2 can ablate, necrose, cut, infuse, inject, stitch, join, coagulate, retract, or clamp a tissue or portion of a tissue. The RF ablator tip 2 can sense, detect, or measure one or more of the following: an electrophysiological, neurological, or physical signal; a tissue structure dimension; a tissue composition; a tissue property; a tissue presence; a tissue contact state or parameter; or a body fluid parameter. In addition, the RF ablator tip 2 can provide an electrophysiological or neurological stimulation. In an embodiment, the fiber 5 terminus adjacent to the gap 6 defines the proximal reflective wall of the resonant etalon or FP cavity. Collimated or non-collimated light emanating from fiber 5 can be reflected from a distal reflective surface or mirror 14, shown to good advantage in the cross-sectional view of FIGS. 2N-2Q. Mirror 14 can be located closely adjacent to proximal reflective wall and can be suspended from the inner surface of the catheter walls by two or more legs, stakes, or similar support structures 15. Mirror 14 can be located centrally or off-center in spring section 3B or the distal tip 2 of catheter 1B. Additionally, mirror 14 can have a larger diameter than that of the fiber 5 terminus, so as to receive light beams when catheter 1B is deflected and there is a wedge angle between mirror 14 and fiber 5 terminus. In an embodiment, flexible structure 3A'/3B'/3C' can be used instead of mirror 14 as a reflective surface of the FP cavity.

In an embodiment, at least one of the proximal or distal reflective walls of the FP cavity can be provided by the etching, dissolving, or subtractive localized removal of a cavity spacer material layer, the thickness of which is equal to the desired cavity thickness. Furthermore, the gap 6 between the proximal and distal reflective walls can be determined by spacer spherical microparticles of precisely controlled and uniform diameter.

The flexible structure 3A'/3B'/3C' can have three sections, 3A', 3B', and 3C', with 3C' being a pre-calibrated compliant section. In the presently described embodiment, only one optically reflective gap 6 is needed. Furthermore, the compliant flexible structure section 3C' in FIGS. 2A and 2B deflects only a small amount (between about 0.6 degrees and about 10 degrees at the maximum, depending on whether a SMF or MMF FP is employed) at the maximum expected tissue load.

Compliant flexible structure section 3C' in FIGS. 2A and 2B can be a single circumferentially wrapped spring-like structure comprising laser-etched slots 11 in a piece of nitinol tubing, for example. The slots 11 can also be etched via electrical discharge machining, chemical or plasma etching, or a machining tool, for example. The compliant flexible structure section 3C' shown in the example depicted in FIG. 2B includes many 45 degree beams, which can undergo axial as well as bending deflection yet are quite stiff as a group. A single laser pattern can be used to attain the desired axial and bending stiffness of compliant flexible structure section 3C'. Many different lasered patterns and/or flexible materials can be used to make compliant flexible structure section 3C'. For example, compliant flexible structure section 3C' can comprise cross-hatched slots or beams, a close array of holes, a helical cut hypotube, a laser-cut helical spring, a braided shaft, elastic materials or structures, or any combination of the above, as shown in FIGS. 2C-2L. Still other examples of flexible neck regions that can comprise compliant flexible structure section 3C' include those disclosed in patent application publication numbers US2009/0254078 A1 and US2011/0270046 A1, both of which are commonly owned and incorporated herein by reference in their entirety. The above described formats of compliant flexible structure section 3C' can allow for equalization of the bending forces in all off-axis directions and in compression.

Referring again to FIGS. 2A and 2B, a gap 6 can be located inside of the compliant flexible structure section 3C'. The gap 6 can act as the reflection cavity of the FP sensor. Note that for the single-sensor FP device of FIGS. 2A and 2B, there are no side-slots (such as 6A and 6B of FIG. 1A), each with its own FP sensor; instead there is a single interior gap 6 centered on the axis of the catheter tip and a single FP sensor/fiber 5 running down the center axis of the catheter 1B. The force-calibrated compliant flexible structure section 3C' comprising the many circumferential laser-etched slots 11 provides both the axial and bending compliance needed for force sensing via a single-fiber FP sensor.

Sensors 10 (shown in phantom in FIGS. 2A and 2B) are not FP sensors; rather, sensors 10 are other types of sensors, such as ultrasonic lesion-feedback sensors, which can now be fit into the tip 2 because the single-fiber FP force sensor is much reduced in size and complexity compared to triaxial sensors. FIG. 2B also shows some electrical (or even optical) interconnections 12 running to/from the other sensors 10 across the flexible structure 3A'/3B'/3C', as the single-fiber FP force sensor allows room for such interconnections 12. The compliant flexible structure section 3C' is not easily interfered with by interconnections 12 or tubing running through its interior. Furthermore, all such interconnections 12 or lumens can be protected by placing them inside the compliant flexible structure section 3C' (unlike the prior FP force art of FIGS. 1A and 1B).

FIGS. 2C-2L depict different exemplary materials and patterns that can be used for the compliant flexible structure section 3C' of the single-fiber FP force sensor of FIGS. 2A and 2B. As discussed above with respect to FIGS. 2A and 2B, the different materials and patterns that can be used for the compliant flexible structure section 3C' are all designed to permit axial and bending deflection while maintaining a desired degree of stiffness.

Figure 2C:
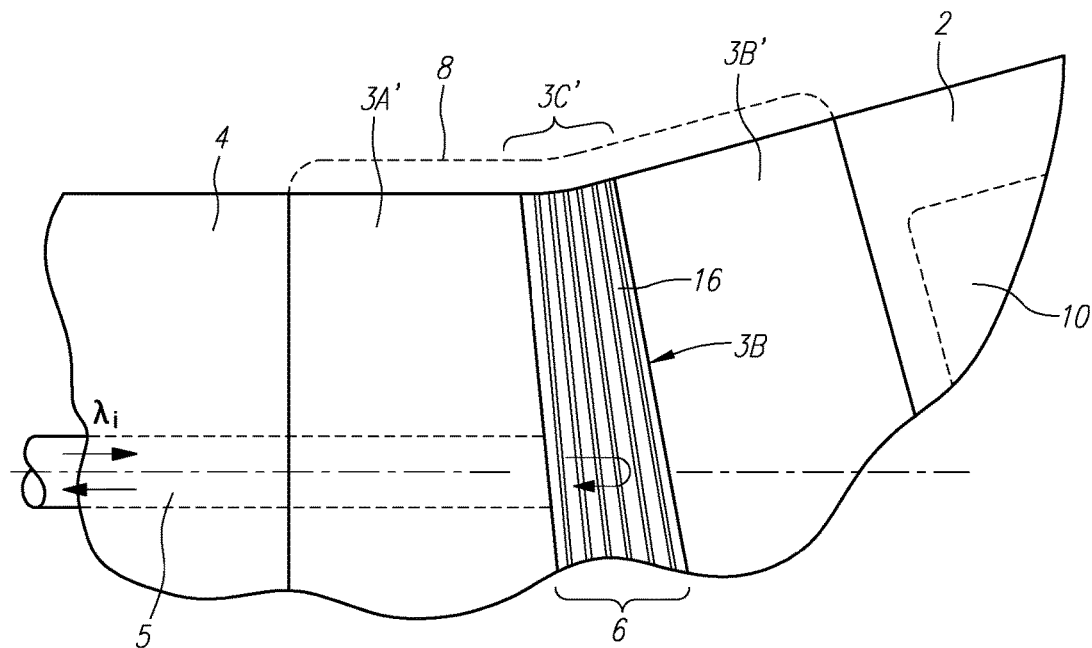
FIGS. 2C-2L are schematic views of different exemplary materials and patterns that can be used for the compliant flexible structure section 3C' of the single-fiber FP force sensor of FIGS. 2A and 2B in accordance with the present disclosure.
Figure 2D:
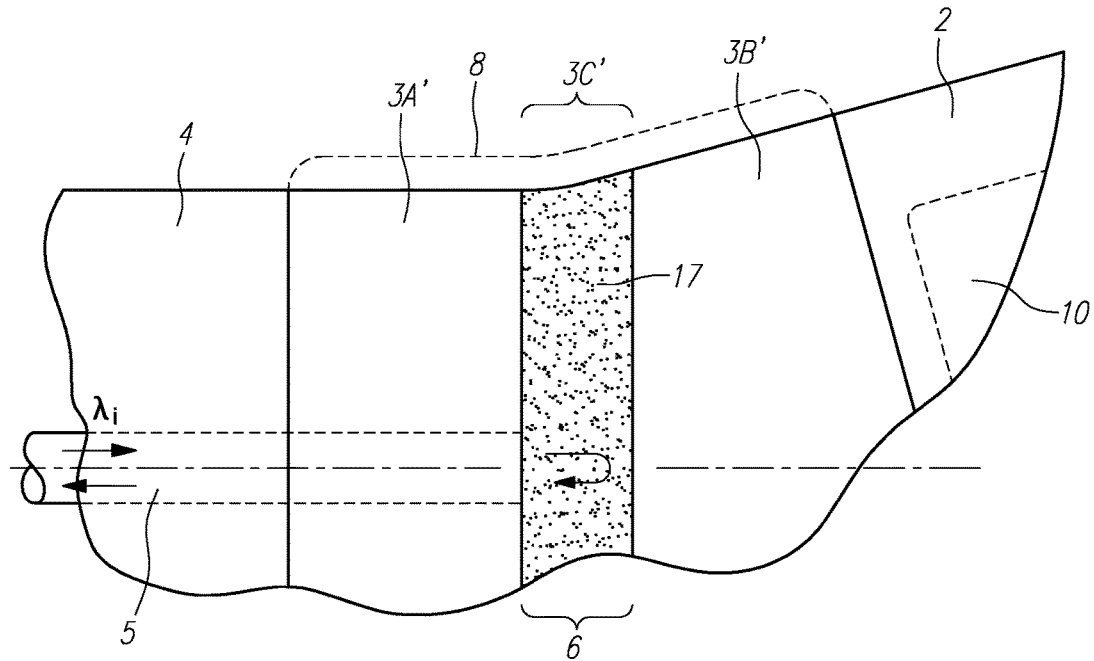
Figure 2E:
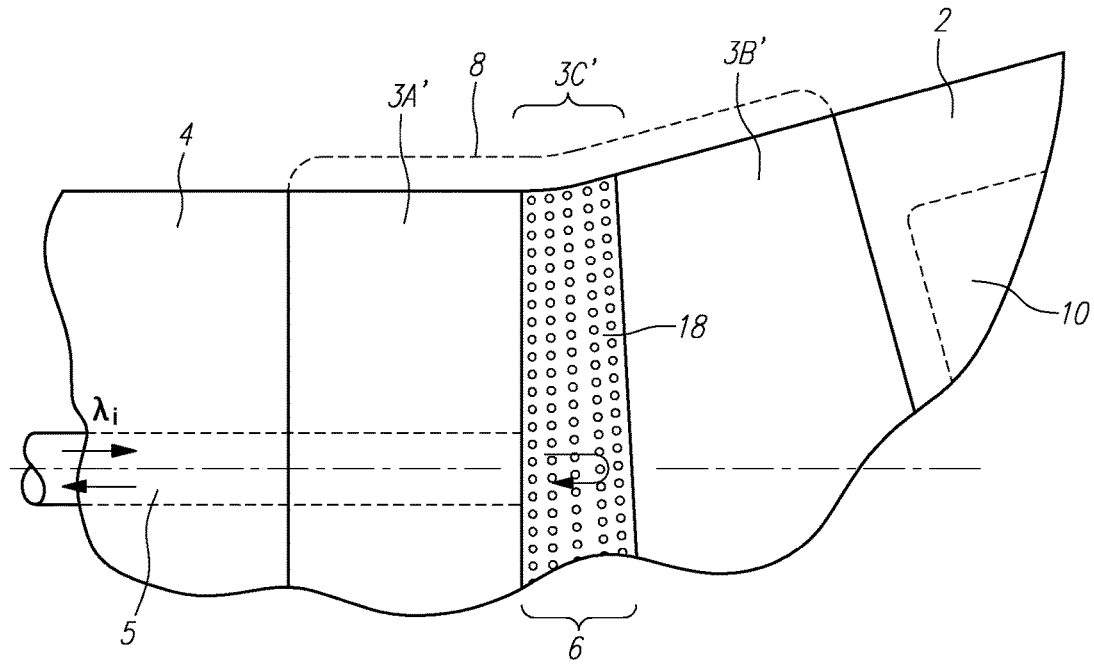
Figure 2F:
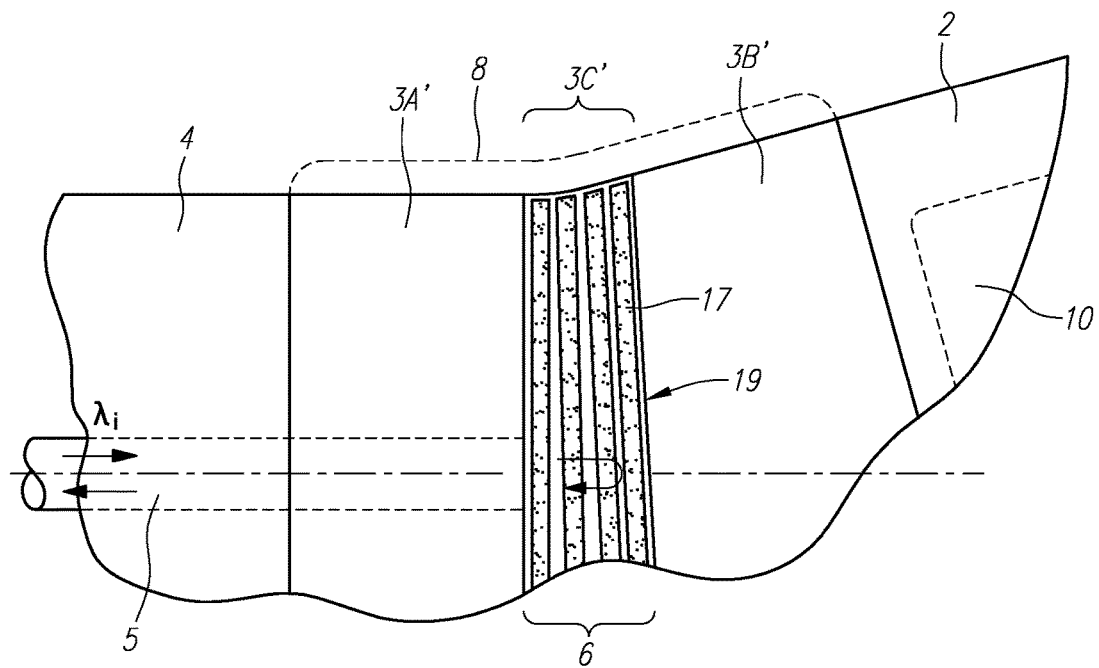
Figure 2G:
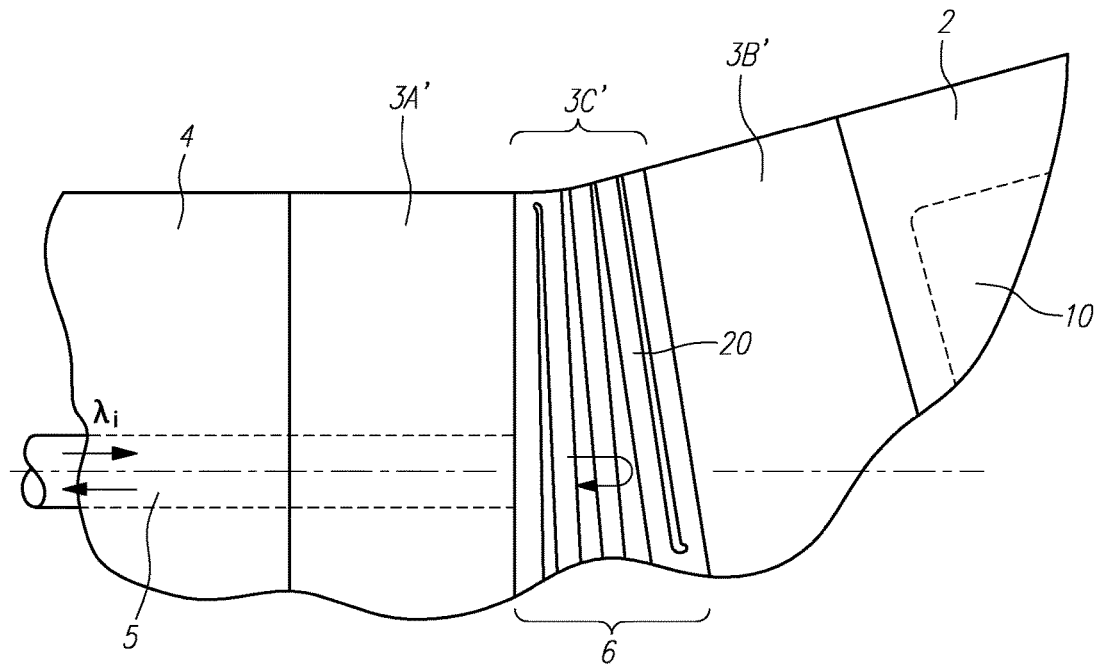
Figure 2H:
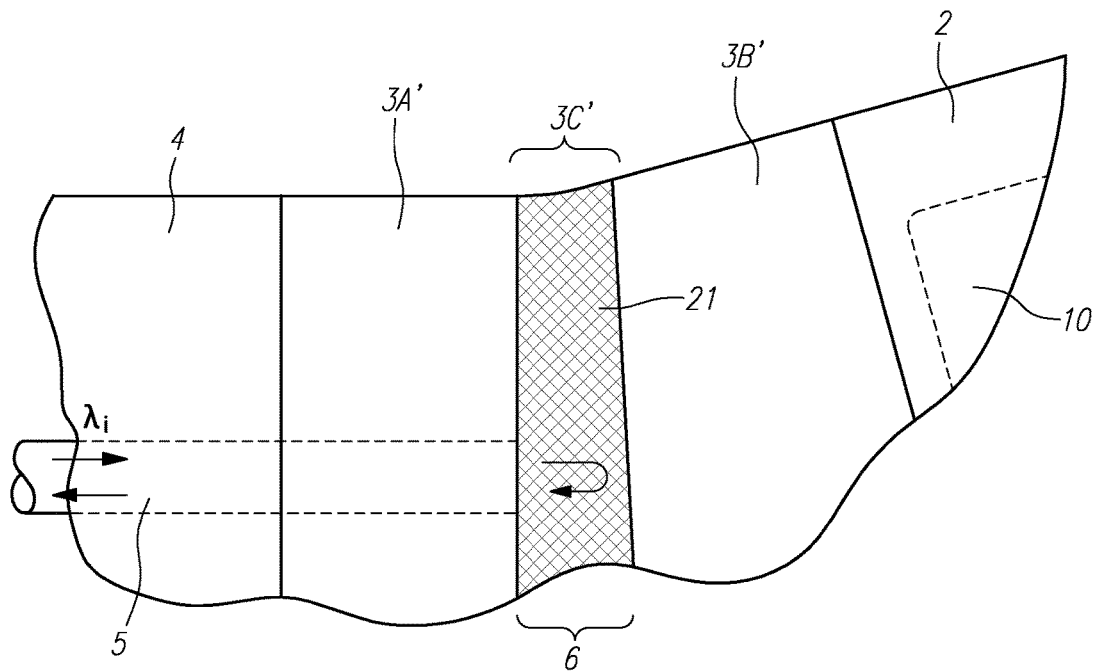
Figure 2I:
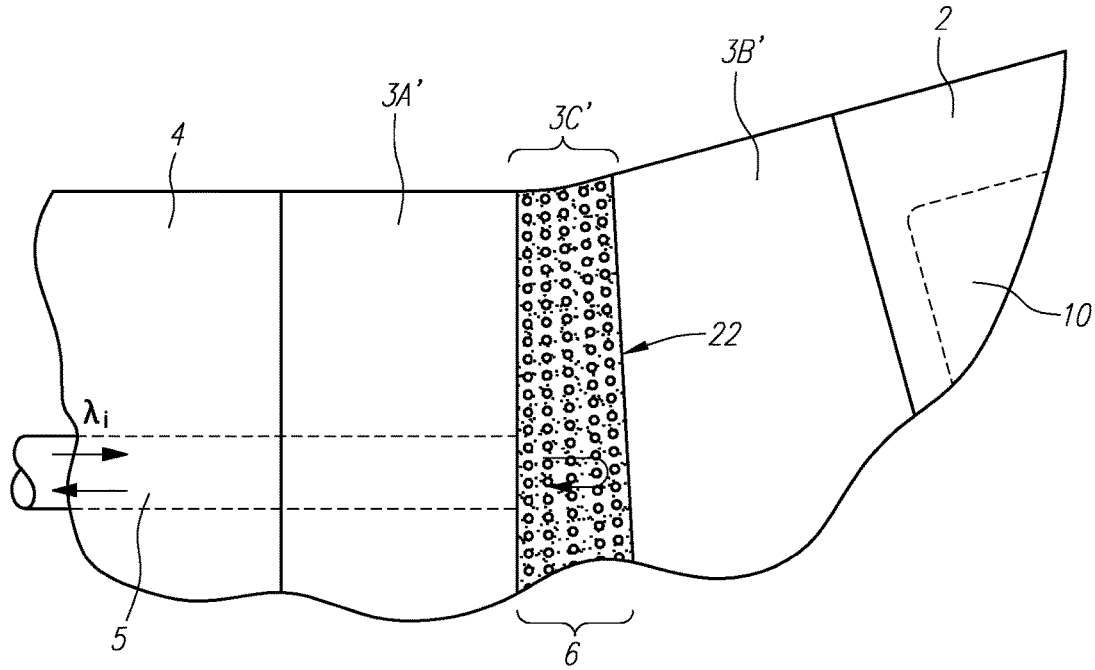

In FIG. 2C, a helical-cut hypotube 16 comprises the compliant flexible structure section 3C'. The helical-cut hypotube 16 can be fabricated from, for example, stainless steel or nitinol tubing and can be laser-cut. FIG. 2D depicts an elastic material 17 comprising compliant flexible structure section 3C'. Examples of such elastic materials 17 include conductive silicones or other elastomers. FIG. 2E depicts a close array of holes 18 comprising compliant flexible structure section 3C'. The close array of holes 18 can be laser-cut from materials such as stainless steel or nitinol. FIG. 2F depicts elastic material 17 deposited in a pattern of laser-etched slots 19 comprising compliant flexible structure section 3C'. FIG. 2G depicts a laser-cut spring 20, which can be made of stainless steel or nitinol comprising compliant flexible structure section 3C'. FIG. 2H depicts a pattern of cross-hatched slots or beams 21 made of stainless steel or nitinol comprising compliant flexible structure section 3C'. FIG. 2I depicts compliant flexible structure section 3C' comprising a combination 22 of elastic material 17 and a close array of holes 18.

Figure 2J:
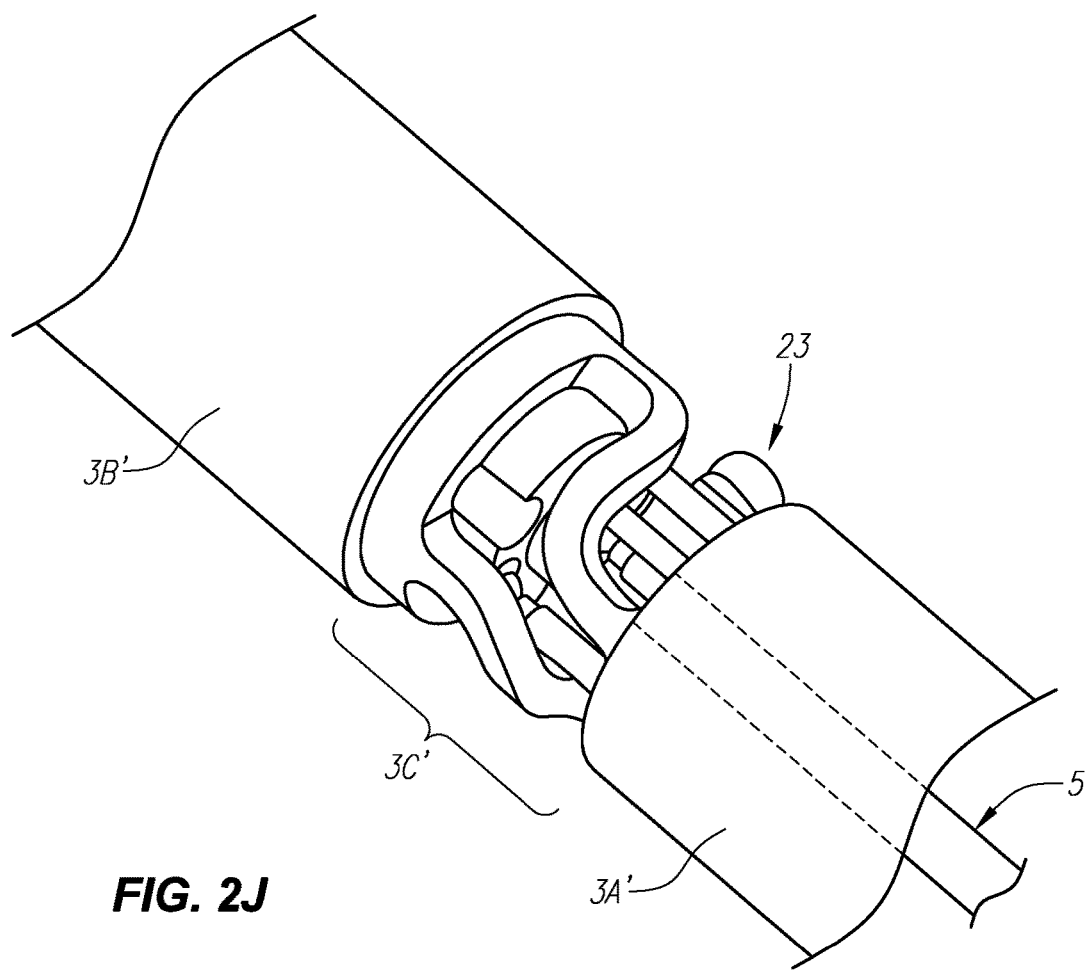
Figure 2K:
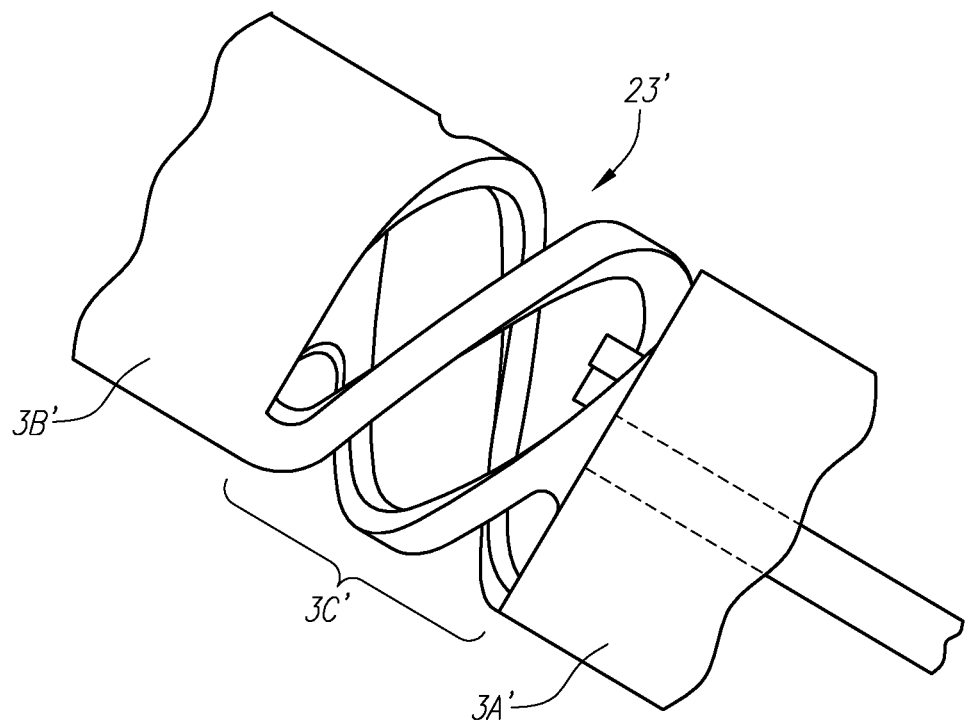
Figure 2L:
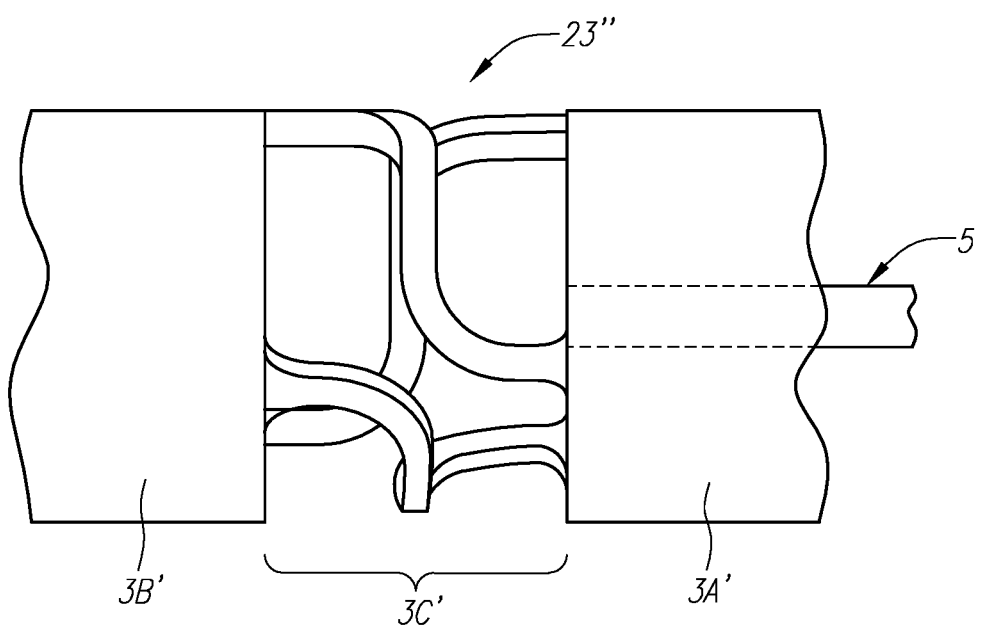

FIGS. 2J, 2K, and 2L show examples of flexible neck regions that can comprise compliant flexible structure section 3C', such as those disclosed in patent application publication US 2011/0270046 A1 FIGS. 2J, 2K, and 2L depict coupling members 23, 23', and 23", respectively, which can comprise or include elastic or other flexible materials, such as stainless steel or nitinol. Coupling members 23, 23', or 23" can comprise compliant flexible structure section 3C'.

Figure 2M:
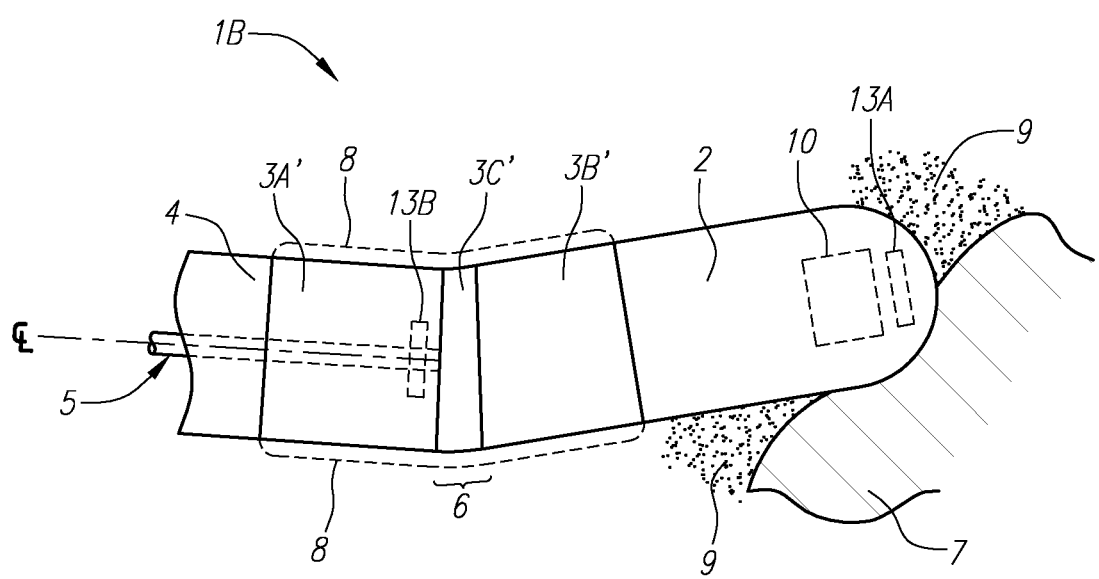
FIG. 2M is a schematic view of an exemplary force sensing catheter including magnetic coils that can be used for localization and navigation of the catheter in accordance with the present disclosure.

FIG. 2M depicts the single fiber 5 optical FP sensor of catheter 1 with force-calibrated compliant flexible structure 3A'/3B'/3C', as in FIG. 2A. In addition, catheter 1B contains magnetic sensor 13A located in the tip 2 and magnetic sensor 13B located proximal to compliant spring section 3C'. These magnetic sensors 13A and 13B can be used to locate and track catheter 1B in a 3D space, such as by using Medi-Guide™ technology, as described in U.S. Pat. No. 7,386,339, which is commonly owned and incorporated herein by reference in its entirety.

Figure 2N:
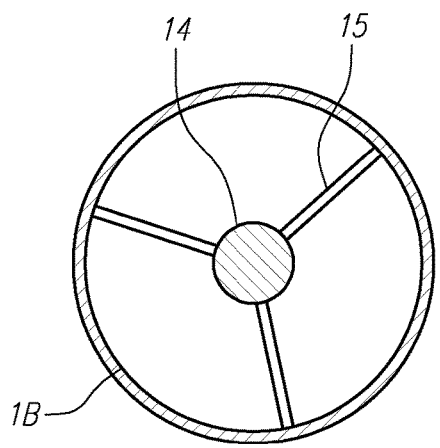
FIGS. 2N-2Q are cross-sectional view of exemplary embodiments of the catheter shown in FIG. 2A in accordance with the present disclosure.
Figure 2O:
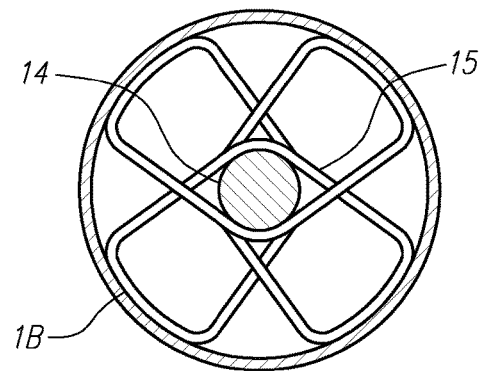
Figure 2P:
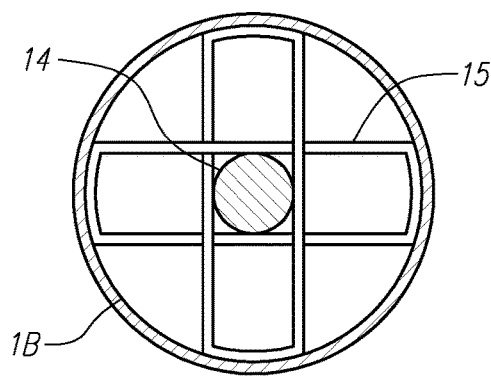
Figure 2Q:
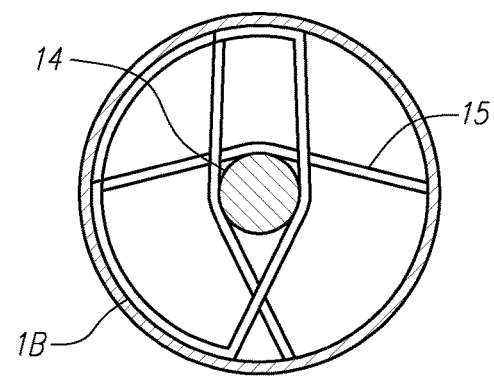
Figure 3:
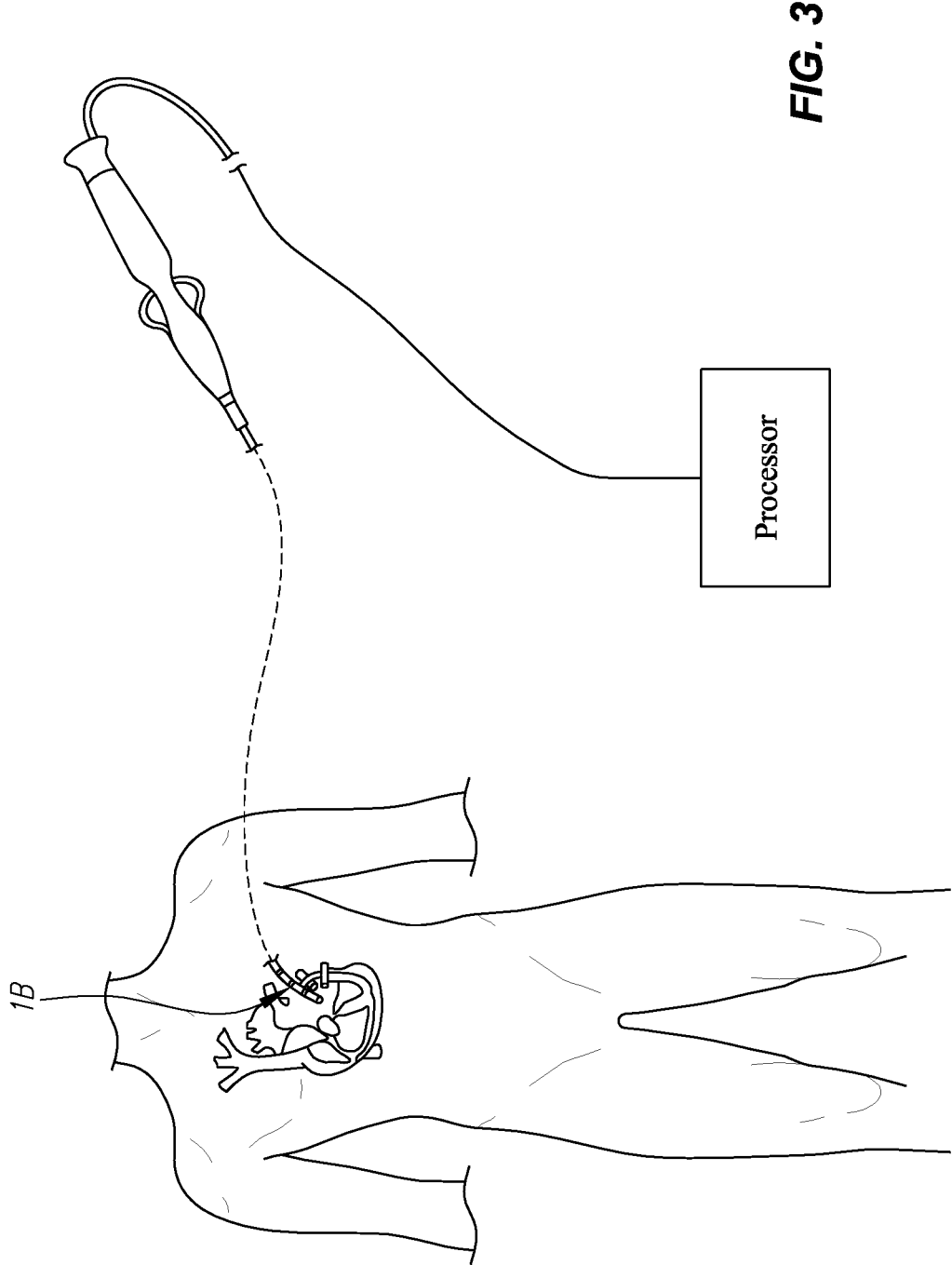
FIG. 3 is a schematic view depicting an ablation catheter in use in a patient and connected to a processor, in accordance with the present disclosure.

FIGS. 2N-2Q are exemplary embodiments of a cross-sectional view of the catheter 1B shown in FIG. 2A. As described above with respect to FIG. 2A, collimated or non-collimated light emanating from fiber 5 can be reflected from a distal reflective surface or mirror 14. Mirror 14 can be suspended from the walls of catheter 1B by two or more legs, stakes, or similar support structures 15, as shown in FIG. 2N. Support structures 15 can be arranged in various manners, as seen in FIGS. 2O-2Q. Again, mirror 14 can be located centrally or off-center in flexible structure section 3B' or the distal tip 2 of catheter 1B. Finally, mirror 14 can have a larger diameter than that of the fiber 5 terminus, so as to receive light beams when catheter 1B is deflected and there is a wedge angle between mirror 14 and fiber 5 terminus.

As mentioned above with respect to FIGS. 1A and 1B, the measurable parameter used to detect tilt angle (catheter tip bend angle) is called fringe visibility (or fringe contrast) and is defined as:

$$V_b = (I_{max} - I_{min})/(I_{max} + I_{min})$$

where $V_b$ is the fringe visibility (or contrast) and $I_{max}$ and $I_{min}$ are the maximum and minimum spectral intensities of the spectral fringes of the FP sensor.

Fringe visibility is related to gap length, and wedge angle for a SMF FP sensor. In general, fringe visibility decreases as gap length increases. However, most single-fiber FP sensors have a gap length less than 100 μm, and the visibility degradation owing to the gap length is acceptable for most practical applications. Furthermore, fringe visibility generally decreases as wedge angle increases.

Prior studies have shown that a SMF FP sensor having a gap dimension of 60 to 80 μms, displays a fringe visibility reduction or change of about 65% over a wedge angle range of 0-5 degrees (see Han, FIG. 2.7). Assuming that the wedge angle is proportional or equal to the actual catheter tip bending angle, this change in fringe visibility can be used to measure of bending deflection, from which bending force can be calculated.

Up until this point, wedge angles have been discussed primarily with respect to SMF FP sensors. The prior art has shown that MMF FP sensors have a similar wedge effect, but it is over a total angular range which is generally smaller than for SMF FP sensors. That is, the MMF FP sensors allow a total angular range of about 1-2 degrees (see, e.g., Han, Chapter 4), whereas SMF FP sensors allow a total angular range of up to about 10 degrees. Thus, any initial nonzero wedge angle affects MMF-FP sensors much more than SMF-FP sensors. This can be regarded as an advantage in the case wherein only about 1 degree of total bending is allowed by the application, there is still a large fringe visibility fall off assuming zero initial wedge angle. This can be regarded as a disadvantage, however, if more than about 5 degrees of bend excursion is allowed by the application; in this case, it may be simpler to utilize a SMF-FP sensor and get the same approximate fringe contrast reduction with an easier-to-build sensor.

Alternative signal processing methods that can be employed to measure and track axial and bending forces during an RF ablation procedure. For example, one approach may be to record look-up tables of normalized fringe visibility, null positions, and spectral shapes derived from a factory calibration procedure. The best-fit axial and bending forces may then be determined in real time by interpolation. A known automatic 'zeroing' method could also be used to normalize the peak reflectivities, which can be affected by light source variations, connector losses, and environmental degradation of reflective surfaces, among other factors.

Although embodiments of a single-fiber force sensing catheter have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various embodiments have been described above to various apparatuses, systems, and/or methods. Numerous specific details have been set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated above are non-limiting examples, and thus it can be appreciated that the specific structural and functional details disclosed above may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment.

Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" have been used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" have been used above with respect to the illustrated embodiments. However, surgical instruments may be used in many orientations and positions, and these terms are not intended to be limiting and absolute.

What is claimed is:

1. A force-sensing assembly comprising:
   a catheter shaft comprising a proximal section and a distal section, the distal section comprising a distal tip portion, wherein the distal tip portion comprises ablation electrode;
   a flexible structure located adjacent the distal tip portion, the flexible structure having a calibratable stiffness;
   no more than one optical fiber extending longitudinally along at least a portion of the catheter shaft and defining a first Fabry-Perot reflective surface adjacent to the flexible structure, the optical fiber configured to communicate optical interference data; and
   a second Fabry-Perot reflective surface located closely adjacent to the first Fabry-Perot reflective surface, wherein the first and second Fabry-Perot reflective surfaces are separated by a gap comprising part of the flexible structure and configured to facilitate relative movement between the first and second Fabry-Perot reflective surfaces when the distal section of the catheter shaft is deflected.

2. The force-sensing assembly of claim 1, wherein the first Fabry-Perot reflective surface and the second Fabry-Perot reflective surface together comprise a Fabry-Perot interferometer.

3. The force-sensing assembly of claim 1, wherein the first and second Fabry-Perot reflective surfaces are separated by a wedge angle.

4. The force-sensing assembly of claim 3, wherein the flexible structure is configured to enable the wedge angle to vary between about 0.0 degrees and about 10 degrees.

5. The force-sensing assembly of claim 1, wherein the single optical fiber is configured to be axially centered within the catheter shaft in a region adjacent to a proximal side of to the flexible structure.

6. The force-sensing assembly of claim 1, wherein a diameter of the second Fabry-Perot reflective surface is greater than a diameter of the first Fabry-Perot reflective surface.

7. The force-sensing assembly of claim 1, wherein the gap is between about 60 microns and about 80 microns.

8. The force-sensing assembly of claim 1, further comprising a processor configured to use the optical interference data and the calibrated stiffness of the flexible structure to determine at least an axial force and a bending force at the distal tip portion of the catheter.

9. The force-sensing assembly of claim 1, wherein the calibrated stiffness of the flexible structure includes a calibrated axial stiffness and a calibrated bending stiffness.

10. The force-sensing assembly of claim 1, wherein the optical interference data includes an optical interference fringe spacing and an optical interference fringe visibility;
    wherein the optical interference fringe spacing corresponds to an axial deflection of the distal tip portion of the catheter; and
    wherein the optical interference fringe visibility corresponds to a bending deflection of the distal tip portion of the catheter.

11. The force-sensing assembly of claim 1, wherein the flexible structure comprises a flexible annular band oriented transverse to a longitudinal axis of the catheter shaft.

12. The force-sensing assembly of claim 11, wherein the flexible annular band spans an entire circumference of the catheter shaft.

13. The force-sensing assembly of claim 1, wherein the flexible structure comprises a metal tube with a laser-cut pattern, the laser-cut pattern comprising at least one of a plurality of angled slots, a plurality of cross-hatched slots, a plurality of closely-arrayed holes, and at least one helical spring.

14. The force-sensing assembly of claim 1, wherein the flexible structure comprises an elastic material.

15. The force-sensing assembly of claim 1, wherein the catheter further comprises at least a first position sensor and a second position sensor, wherein the first position sensor is located adjacent to the distal tip portion of the catheter, and wherein the second position sensor is located proximal to the flexible structure.

16. A force-sensing assembly comprising:
    a catheter shaft comprising a proximal section and a distal section, the distal section comprising a distal tip portion;
    a flexible structure located adjacent the distal tip portion, the flexible structure having a calibratable stiffness;
    no more than one optical fiber extending longitudinally along at least a portion of the catheter shaft and defining a first Fabry-Perot reflective surface adjacent to the flexible structure, the optical fiber configured to communicate optical interference data;
    a second Fabry-Perot reflective surface located closely adjacent to the first Fabry-Perot reflective surface, wherein the first and second Fabry-Perot reflective surfaces are separated by a gap comprising part of the flexible structure and configured to facilitate relative movement between the first and second Fabry-Perot reflective surfaces when the distal section of the catheter shaft is deflected; and
    a processor configured to use the optical interference data and the calibrated stiffness of the flexible structure to determine at least an axial force and a bending force at the distal tip portion of the catheter;
    wherein the first Fabry-Perot reflective surface and the second Fabry-Perot reflective surface together comprise a Fabry-Perot interferometer;
    wherein the first and second Fabry-Perot reflective surfaces are separated by a wedge angle between about 0 degrees and 10 degrees;
    wherein the detected optical interference data includes an optical interference fringe spacing and an optical interference fringe visibility;

wherein the optical interference fringe spacing corresponds to an axial deflection of the distal tip portion of the catheter; and wherein the optical interference fringe visibility corresponds to a bending deflection of the distal tip portion of the catheter.

17. A force-sensing assembly comprising:

a catheter shaft comprising a proximal section and a distal section, the distal section comprising a distal tip portion;

a flexible structure located adjacent the distal tip portion, the flexible structure having a calibratable stiffness;

no more than one optical fiber extending longitudinally along at least a portion of the catheter shaft and defining a first Fabry-Perot reflective surface adjacent to the flexible structure, the optical fiber configured to communicate optical interference data;

a second Fabry-Perot reflective surface located closely adjacent to the first Fabry-Perot reflective surface, wherein the first and second Fabry-Perot reflective surfaces are separated by a gap comprising part of the flexible structure and configured to facilitate relative movement between the first and second Fabry-Perot reflective surfaces when the distal section of the catheter shaft is deflected; and a processor configured to use the optical interference data and the calibrated stiffness of the flexible structure to determine at least an axial force and a bending force at the distal tip portion of the catheter.

* * * * *